United States Patent [19]

Schmidt et al.

[11] Patent Number: 4,863,688

[45] Date of Patent: Sep. 5, 1989

[54] METHOD OF DECONTAMINATING SURFACES ON OR NEAR LIVING CELLS WITH VAPOR HYDROGEN PEROXIDE

[75] Inventors: William C. Schmidt, Edinboro; James R. Rickloff, Erie, both of Pa.

[73] Assignee: American Sterilizer Company, Erie, Pa.

[21] Appl. No.: 948,368

[22] Filed: Dec. 31, 1986

[51] Int. Cl.$^4$ .............................................. A61L 2/20
[52] U.S. Cl. ..................................... 422/28; 422/110; 424/616; 426/320; 435/2; 435/240.1; 435/244; 435/311
[58] Field of Search ................. 422/28, 110; 424/130; 426/320; 435/2, 240.1, 311, 244

[56] References Cited

U.S. PATENT DOCUMENTS

| | | | |
|---|---|---|---|
| 3,954,974 | 5/1976 | Herzog et al. | 424/130 |
| 4,169,123 | 9/1979 | Moore et al. | 422/32 X |
| 4,169,124 | 9/1979 | Forstrom et al. | 422/32 X |
| 4,670,223 | 6/1987 | Delachapelle | 422/4 X |
| 4,681,738 | 7/1987 | Low | 422/28 |

OTHER PUBLICATIONS

Bradley et al., Biochimica et Biophysica Acta, 654:135-141.
Carlsson et al., Infection and Immunity, Jun. 1984:581-586.
Jones et al., British J. of Cancer, 52:583-590.
Peterkofsky et al., J. Cell Physiology, 90:61-70.

Primary Examiner—Barry S. Richman
Assistant Examiner—Jill Johnston
Attorney, Agent, or Firm—Kirkpatrick & Lockhart

[57] ABSTRACT

A method of selectively destroying organisms within a predetermined area is comprised of the steps of introducing vapor phase hydrogen peroxide into the predetermined area at a rate sufficient to cause a predetermined concentration of hydrogen peroxide to be reached while preventing any substantial change in pressure or condensation of the hydrogen peroxide within the predetermined area. The predetermined concentration is maintained for a period of time sufficient for destroying undesirable organisms but insufficient for harming desirable organisms. When the predetermined period of time has elapsed, the vapor phase hydrogen peroxide is removed from the area.

18 Claims, 3 Drawing Sheets

METHOD OF DECONTAMINATING SURFACES ON OR NEAR LIVING CELLS WITH VAPOR HYDROGEN PEROXIDE

BACKGROUND OF THE INVENTION

1. Field of the Invention

The present invention is related generally to decontamination procedures and more specifically to decontamination procedures carried out using vapor phase hydrogen peroxide.

Contamination by microorganisms is one of the most troublesome problems encountered today by people growing tissue cultures. Contamination wastes time and money, and causes the loss of valuable tissue cultures. In addition to contamination problems, plant tissue culturists face problems stemming from the practice of "disinfesting" plant cells prior to culturing. Currently, there is no convenient method for disinfesting plant tissue without risking damage to the plant tissue itself.

No known methods exist for the decontamination of tissue culture incubators with the cultures in place, i.e. in situ decontamination, because known decontamination procedures, e.g. steam or ethylene oxide treatments, would destroy the cultures. Because of this lack of an ability to perform in situ decontamination, various technics have been employed to minimize the chances of tissue culture contamination. Incubators have been designed to provide vertical laminar air flow over the culture containers. This laminar air flow helps to keep airborne contaminants from coming into contact with the tissue cultures. One manufacturer has developed an incubator with copper walls which possesses germicidal and fungicidal properties under the proper conditions. Such an incubator cannot, however, destroy contaminants in the air, on the shelving, or on the various tissue culture containers. In the past, antibiotics have been added to tissue cultures to prevent contamination. However, genetic or metabolic changes can occur in the cells and it is now desirable to avoid adding antibiotics to the growth medium when at all possible. Thus, a need exists for a method which will enable the decontamination of tissue culture incubators with the cultures in place.

Plant cell culturists are currently required to use crude methods to disinfest plant cells prior to culturing experiments. Current practices involve soaking samples in dilute Chlorox (1%), glutaraldehyde, or ethanol for up to thirty minutes. Many plant cells cannot be exposed to these disinfectants. However, no real alternatives exist. Trial and error is the general rule employed to obtain pure cultures. Thus the need exists for a method which will enable plant cell culturists to disinfest plant cells prior to culturing experiments.

It is known that even low concentrations of vapor phase hydrogen peroxide can be effective for decontamination and sterilization. Although vapor phase hydrogen peroxide has been used in the past for such purposes, such uses have not involved living cells. For example, see Coulter U.S. Pat. No. 2,193,622 entitled "Preserving Bakery Products", Moore, et al. U.S. Pat. No. 4,169,123 entitled "Hydrogen Peroxide Vapor Sterilization Method", and Forstrom, et al. U.S. Pat. No. 4,169,124 entitled "Cold Gas Sterilization Process". In each of these patents, vapor phase hydrogen peroxide is used for sterilization but not in an environment containing living tissue.

Liquid phase hydrogen peroxide has been used around immobilized whole cells for the purpose of providing increased oxygenation, not for the purpose of decontamination. Holst, "Hydrogen Peroxide as an Oxygen Source for Immobilized Gluconobacter oxydans", Applied Microbiology and Biotechnology 22, pages 383–388. The major disadvantage of this process is that the hydrogen peroxide concentration in the liquid phase (34 mg/l) destroyed a majority of the cells prior to enzymatic decomposition of the hydrogen peroxide into oxygen and water.

Clearly, the need exists for a convenient method of in situ decontamination and a method for disinfesting plant cells prior to being cultured.

SUMMARY OF THE PRESENT INVENTION

The present invention is a method of selectively destroying organisms within a predetermined area thereby enabling in situ decontamination. Vapor phase hydrogen peroxide is introduced into the predetermined area at a rate sufficient to cause a predetermined concentration of hydrogen peroxide to be reached while preventing any substantial change in pressure or condensation of the hydrogen peroxide within the predetermined area. The predetermined concentration of hydrogen peroxide is maintained for a period of time sufficient for destroying the undesirable organisms. The vapor phase hydrogen peroxide is then removed from the area after the period of time has elapsed and before desirable living cells in vitro are harmed by the hydrogen peroxide.

The method of the present invention may be used in conjunction with enclosures such as incubators and autoclaves. The method of the present invention allows for the decontamination or sterilization of all exterior surfaces within the enclosed area including the surfaces of the containers carrying the tissue cultures, as well as the destruction of microorganisms in the air within the enclosure. However, exposure times and hydrogen peroxide concentrations are controlled such that tissue cultures are not affected by the vapor phase hydrogen peroxide.

According to one embodiment of the present invention it is anticipated that the desirable living cells or organisms will be held in containers, with each container having a tortuous path at its opening. The predetermined concentration of vapor phase hydrogen peroxide and the time during which the predetermined concentration is maintained is monitored such that the hydrogen peroxide has insufficient time to travel the tortuous path and reach the living cells.

According to another embodiment of the present invention it is anticipated that the desirable living cells will be held in containers, with each container having a filter at its opening. The predetermined concentration of vapor phase hydrogen peroxide and the time during which the predetermined concentration is maintained is monitored such that the hydrogen peroxide has insufficient time to travel through the filter and reach the living cells.

In yet another embodiment of the present invention desirable living cells are held in open containers. The predetermined concentration of vapor phase hydrogen peroxide and the time during which the predetermined concentration is maintained are monitored such that the hydrogen peroxide disinfests the desirable living cells without harming them.

The method of the present invention for selectively destroying organisms within a predetermined area is comprised of the following steps. An air flow is established through the predetermined area. The temperature of the flowing air is measured. The maximum rate of injection of vapor phase hydrogen peroxide into the predetermined area is calculated based on the measured temperature. The concentration of a source of aqueous hydrogen peroxide is ascertained. The liquid hydrogen peroxide drip or flow rate needed to achieve a desired injection rate, which is not greater than the calculated maximum injection rate of vapor phase hydrogen peroxide, is calculated. The aqueous hydrogen peroxide is conveyed at the calculated rate into an apparatus for vaporizing. The rate is maintained for a period of time sufficient to establish a predetermined concentration of vapor phase hydrogen peroxide and to maintain the predetermined concentration for a period of time sufficient to destroy undesirable organisms and insufficient to harm desirable living cells in vitro. The conveying of aqueous hydrogen peroxide into the apparatus for vaporizing is ended while the air flow through the predetermined area is maintained for a period of time sufficient to remove the vapor phase hydrogen peroxide from the predetermined area.

It is anticipated that the present invention will be used commercially in conjunction with numerous types of enclosures including incubators and autoclaves. The present invention will enable the disinfection or sterilization of the interior surfaces of the enclosure, the exterior surfaces of the containers carrying the tissue cultures, and the airspace within the enclosure while the tissue cultures remain in place in the enclosure. Maintaining such a decontaminated or sterilized environment substantially reduces the likelihood of contamination of the tissue cultures.

The present invention can also be used in conjunction with the preparation of plant tissue cultures. Certain plant tissue cultures may be exposed to concentrations of vapor phase hydrogen peroxide which are sufficient for disinfesting the sample but are insufficient to in any way adversely affect the sample. The present invention thus provides an alternative to the disinfesting techniques currently in use today. These and other uses and benefits of the present invention will become apparent from the description of a preferred embodiment hereinbelow.

BRIEF DESCRIPTION OF THE DRAWINGS

In order that the present invention may be clearly understood and readily practiced, preferred embodiments will now be described by way of example only, with reference to the accompanying figures wherein.

DESCRIPTION OF A PREFERRED EMBODIMENT

Figure 1:
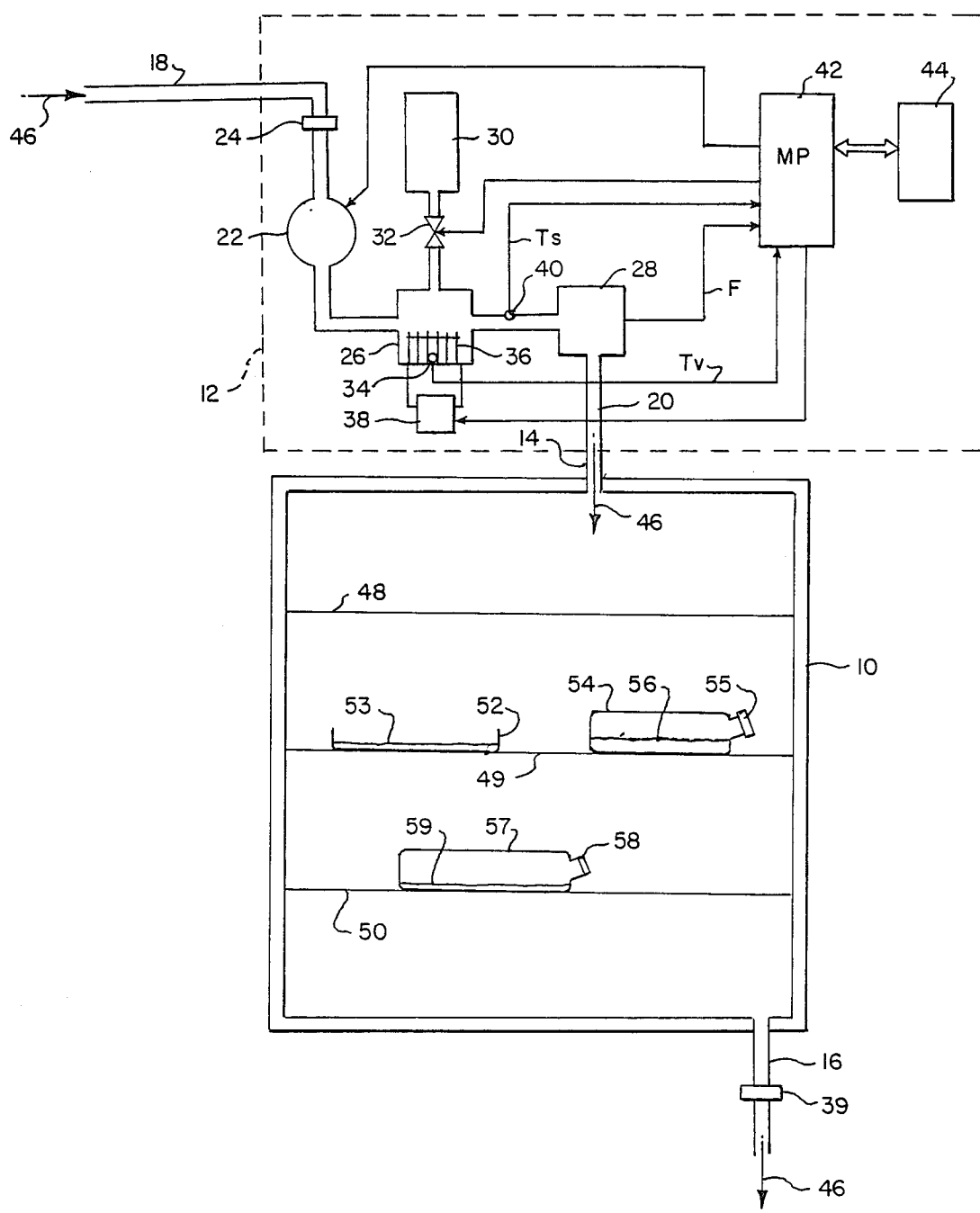
FIG. 1 illustrates an incubator having an apparatus which enables the in situ decontamination method of the present invention to be practiced.

In FIG. 1 an incubator 10 is provided with an apparatus 12 which enables the method of the present invention to be practiced. It should be recognized that although the apparatus 12 (shown within the broken line) is illustrated in FIG. 1 as a separate component from the incubator 10, it is possible that the components comprising the apparatus 12 may be built into the incubator 10. The apparatus 12 is shown with the incubator 10 for purposes of illustration only. The apparatus 12 may be used with an autoclave, or any other type of enclosed, predetermined area.

The incubator 10 may be a conventional type of known incubator having an input tube 14 and an output tube 16. The input tube 14 may receive room air, or any other gas necessary for the purpose for which the incubator is used. The output tube 16 is used to exhaust gases from the incubator 10.

The apparatus 12 has an input tube 18 which receives, in this example, room air. The apparatus 12 has an output tube 20 which is connected to the input tube 14 of the incubator 10.

The input tube 18 is connected to a pump 22 through a sub-micron air filter 24. As an alternative to the pump 22, a device creating a suction may be positioned in output tube 16. The output of the pump 22 is connected to a vaporization chamber 26. The vaporization chamber 26 is connected to the output tube 20 through a flowmeter 28. The vaporization chamber 26 is also connected to a source of liquid phase hydrogen peroxide 30 through a valve 32.

The vaporization chamber 26 contains a temperature sensor 34 as well as a vaporization grid 36 heated by a heat source 38. The heat source 38 may also heat, or preheat, the air stream. The vaporization chamber 26 functions in the following manner. The vaporization grid 36 is maintained at a predetermined temperature by the heat source 38. The predetermined temperature is sufficiently high such that liquid phase hydrogen peroxide is vaporized on contact with the vaporization grid 36. The valve 32 controls the flow of liquid phase hydrogen peroxide from the source 30 which may be, for example, a hydrogen peroxide tank. By controlling the setting of the valve 32, the amount of liquid phase hydrogen peroxide conveyed onto the vaporization grid 36 is controlled. The temperature of the vaporization grid 36 is regulated through the use of the temperature sensor 34. The use of the temperature sensor 34 to regulate the temperature of the vaporization grid 36 as well as the manner in which the valve 32 is controlled is discussed hereinbelow in conjunction with the description of FIG. 2.

The output tube 16 of the incubator 10 contains a hydrogen peroxide filter 39 for removing vapor phase hydrogen peroxide from the exhausted gases.

The apparatus 12 may be manually controlled or may be under the control of a microprocessor 42. The microprocessor 42 receives an input signal Tv from the temperature sensor 34 which is representative of the temperature of the vaporization grid 36, an input signal Ts from a temperature sensor 40 which is representative of the temperature of the air stream represented by arrows 46, and an input signal F from the flowmeter 28 representative of the air flow represented by arrows 46. In addition to these input signals, the microprocessor 42 receives input data from an input device 44. The input data may include the volume of the incubator 10, the concentration of the liquid phase hydrogen peroxide within the container 30, the desired sterilization or decontamination time, and the desired concentration of vapor phase hydrogen peroxide which is to be maintained in the incubator 10. If the apparatus 12 is built into the incubator 10, the microprocessor 42 may be provided with preprogrammed memory which allows the operator to choose between various preset operating conditions. Where the apparatus 12 is a portable device which may be used in conjunction with various different incubators 10 and other enclosures, the input device 44 may take the form of a keypad for inputting the desired information. The manner in which the desired information is input to the microprocessor 42 is considered to be well within the skill of one of ordinary skill in the art such that further description thereof is not considered necessary.

The apparatus 12 enables the decontamination method of the present invention to be carried out while tissue cultures are being incubated within the incubator 10. In FIG. 1, the incubator 10 is illustrated as having three shelves 48, 49, and 50. Shelf 49 carries two containers 52, 54. Container 52 is an open container having a tissue culture 53 therein. Container 54 is a closed container having a screw-on cap 55 which, when not tightly screwed on, provides a tortuous path for gases. The container 54 contains a tissue culture 56. Shelf 50 carries a closed container 57 having a membrane 58 at its opening which absorbs hydrogen peroxide but which allows essential gases to enter and exit the container 57. The container 57 contains a tissue culture 59.

The open type of container 52 may be used in conjunction with the disinfestation of plant cells or other cells impervious to hydrogen peroxide. The closed container 54 having the tortuous gas path and the closed container 57 having the membrane 58 may be used in conjunction with the incubation of animal cells or other cells which need to be shielded from the hydrogen peroxide. Clearly, other types of containers may be used in conjunction with the present invention.

Figure 2:
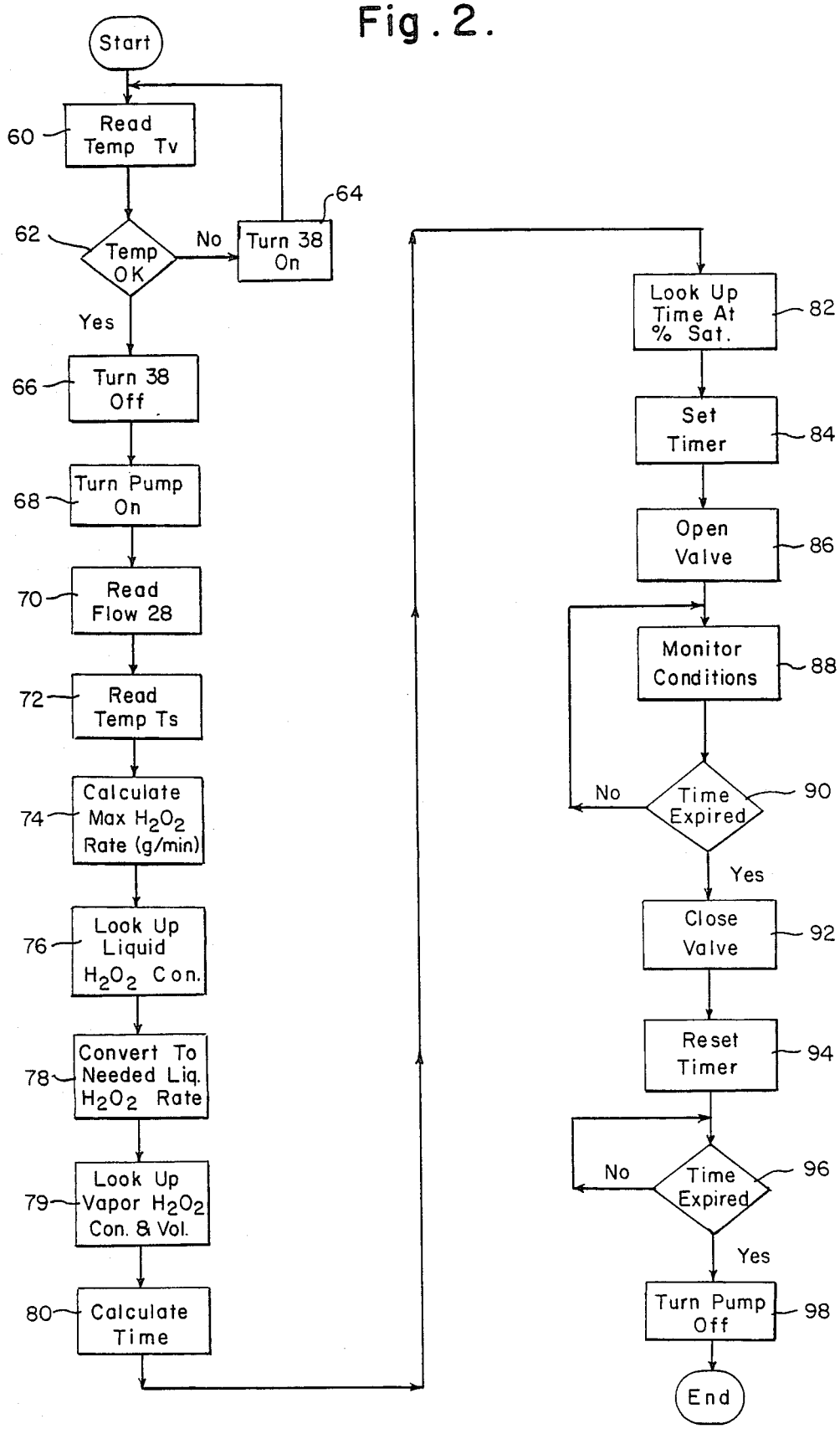
FIG. 2 is a flow chart illustrating the steps involved in carrying out the method of the present invention.

Turning now to FIG. 2, the steps which enable the present invention to be carried out are illustrated. The steps illustrated in FIG. 2 may be performed by the microprocessor 42 or may be performed manually. In FIG. 2, at step 60, the temperature signal Tv representative of the temperature of the vaporization grid 36 is read. At decision step 62, a determination is made regarding whether the temperature of the vaporization grid 36 is sufficient. If not, the heater 38 is turned on at step 64 and the temperature Tv is continually monitored until it becomes sufficient for immediate vaporization of liquid phase hydrogen peroxide.

Once the temperature of the vaporization grid 36 reaches its desired level, the heat source 38 may be turned off at step 66. The pump 22 is turned on at step 68 to establish an air flow, indicated by arrows 46, through the vaporization chamber 26 and into the incubator 10. After the pump 22 has been turned on, the signal F produced by the air flow meter 28 which is representative of the flow of air through the vaporization chamber 26 may be read at step 70. As an alternative to having a flowmeter for providing a signal representative of the air flow, the air flow rate can be calculated from data provided by the manufacturer of the pump 22 according to well known equations.

After the flow of air has been read, or calculated, the temperature Ts of the air stream is read from temperature sensor 40 at step 72. Based on the flow rate F and the temperature Ts of the air stream, the theoretical maximum rate at which hydrogen peroxide may be introduced into the incubator 10 is calculated at step 74. This calculation is carried out under the restrictions that hydrogen peroxide should not be introduced into the incubator chamber 10 in amounts which will cause the vapor phase hydrogen peroxide to condense or in amounts which will cause the pressure within the incubator 10 to rise. Should vapor phase hydrogen peroxide be allowed to condense, exposed tissue cultures may be damaged and decontamination may not be uniformly accomplished. If the pressure within the incubator is allowed to rise, hydrogen peroxide vapor may be forced through barriers which were intended to prevent the penetration of hydrogen peroxide. Therefore it is desirable that the rate of introduction of hydrogen peroxide be such that the vapor phase hydrogen peroxide will not condense and that the pressure within the incubator will not rise.

The following equation may be used to calculate the theoretical maximum rate of introduction of hydrogen peroxide:

$$m/t = 0.2427 \, P \, Y \, F/Ts \quad (1)$$

where
m = mass of $H_2O_2$ injected (grams)
t = time (mins)
P = partial pressure of $H_2O_2$- $H_2O$ sol'n (torr)
Y = mole fraction of $H_2O_2$ in $H_2O_2$- $H_2O$ vapor
F = flow rate of air ($ft^3$/hr)
Ts = temperature of airstream (°K.)

In equation 1, the values for the terms P and Y can be looked up from appropriate tables stored in the microprocessor 42. See for example, tables of values for the terms P and Y found in Schumb, et al., *Hydrogen Peroxide*, 1955, pages 226 and 227. Alternatively, values for the terms P and Y can be input through the input device 44 according to the known conditions of the system. The values for the terms F and Ts are read from the flowmeter 28 and temperature sensor 40, respectively. Thereafter, the theoretical maximum mass of hydrogen peroxide injected per unit time can be calculated using equation 1.

If the hydrogen peroxide stored in source 30 could be 100% pure, then the flow rate of aqueous hydrogen peroxide from the source 30 would equal the maximum theoretical rate calculated at step 74. However, because hydrogen peroxide is normally stored at much lower concentrations, the flow rate of the aqueous hydrogen peroxide solution typically must be higher to achieve the injection rate calculated at step 74. For example, if the aqueous hydrogen peroxide has a concentration of 30%, then the flow rate of aqueous hydrogen peroxide must be approximately three times the maximum rate calculated at step 74 to achieve the rate calculated at step 74.

At step 76, the concentration of the liquid phase hydrogen peroxide stored in source 30 is looked up from stored memory or read from input device 44. The theoretical maximum rate in mass per unit time determined at step 74 is converted at step 78, based on the concentration of the hydrogen peroxide contained within the hydrogen peroxide source 30, to the liquid hydrogen peroxide flow or drip rate needed to achieve the desired injection rate calculated at step 74.

Equation 1 has been solved assuming an air stream temperature Ts of 37° C. and the results converted to the required aqueous hydrogen peroxide flow rate needed to achieve the desired injection rate based on a 30% aqueous hydrogen peroxide solution. Table I reproduced hereinbelow illustrates the results. Table I demonstrates that various amounts of a 30% aqueous hydrogen peroxide solution may be conveyed onto the vaporization grid 36 depending on the air flow rate to achieve the theoretical maximum hydrogen peroxide injection rate into the incubator, that is, an injection rate which will insure that the vapor phase hydrogen peroxide does not condense and that pressure does not build up within the incubator.

TABLE I

Maximum Amount of a 30% Solution Which Can Be Vaporized Into An Airstream at 37° C.

| Flow (ft3/hr) | 30% $H_2O_2$ Solution Saturation (mg/min) |
|---|---|
| 1 | 7.2 |
| 5 | 36.2 |
| 10 | 72.4 |
| 15 | 108.6 |
| 20 | 144.8 |

The flow rates of aqueous hydrogen peroxide illustrated in Table I result in a vapor phase hydrogen peroxide concentration of 4.6 mg/1. This can be demonstrated by converting the airstream flow rates into 1/min and dividing that number into the hydrogen peroxide flow rate. The values shown in Table 2 illustrate the maximum flow rate of an aqueous 30% hydrogen peroxide solution for five different flow rates of the air stream. Thus, the valve 32 can be appropriately manipulated under control of the microprocessor 42 to provide the desired liquid hydrogen peroxide flow rate depending upon the result of the calculation in step 74 and the conversion in step 78. Clearly, if the aqueous hydrogen peroxide solution is of a higher concentration, the liquid flow rate will be lower to achieve the same hydrogen peroxide injection rate. Conversely, if the aqueous hydrogen peroxide solution is of a lower concentration, the liquid flow rate will be higher to achieve the same hydrogen peroxide injection rate.

At step 79, the desired concentration of vapor phase hydrogen peroxide i.e. degree of chamber saturation, and the volume of the incubator 10 are looked up. This information may be stored in the microprocessor's memory or may be input through input device 44. The time needed for the vapor phase hydrogen peroxide to reach the desired concentration may be calculated at step 80 using the following equation.

$$t = (-V/F) \ln(1 - C_t/C_{in}) \quad (2)$$

where
t = time to reach desired concentration
V = volume of incubator
F = flow rate
$C_t$ = concentration of $H_2O_2$ in chamber at time t
$C_{in}$ = concentration of $H_2O_2$ in inflowing air.

Assume that at time t=0, $C_t$=0; the only air flowing into the chamber is peroxide laden at constant flow rate F and at constant concentration $C_{in}$; and complete mixing instantaneously within the chamber. (Means for insuring complete mixing within the incubator 10, such as a fan or baffles, may be used if conditions prevent complete mixing from occurring naturally.) Making these assumptions, equation (2) was solved for chambers of three different sizes using the same temperature Ts (37°) and same liquid hydrogen peroxide concentration (30%) as before. The time required for the vapor phase hydrogen peroxide to reach 12.5%, 25%, 50%, and 90% chamber saturation for three different chamber volumes using various air flow rates F is illustrated in Tables II, III, and IV hereinbelow.

TABLE II 3 ft³ Chamber; 37° C.; 30% $H_2O_2$

| Flow (ft³/hr) | Time (hrs) to reach steady state for desired % chamber saturation | | | |
|---|---|---|---|---|
| | 12.5 | 25 | 50 | 90 |
| 1 | 0.40 | 0.86 | 2.08 | 6.91 |
| 5 | 0.08 | 0.17 | 0.42 | 1.38 |
| 10 | 0.04 | 0.09 | 0.21 | 0.69 |
| 15 | 0.03 | 0.06 | 0.14 | 0.46 |
| 20 | 0.02 | 0.04 | 0.11 | 0.35 |

TABLE III 6 ft³ Chamber; 37° C.; 30% $H_2O_2$

| Flow (ft³/hr) | Time (hrs) to reach steady state for desired % chamber saturation | | | |
|---|---|---|---|---|
| | 12.5 | 25 | 50 | 90 |
| 1 | 0.80 | 1.73 | 4.16 | 13.82 |
| 5 | 0.16 | 0.35 | 0.83 | 2.76 |
| 10 | 0.08 | 0.17 | 0.42 | 1.38 |
| 15 | 0.05 | 0.12 | 0.28 | 0.92 |
| 20 | 0.04 | 0.09 | 0.21 | 0.69 |
| $H_2O_2$ Vapor Concentration (mg/l) | 0.58 | 1.15 | 2.30 | 4.14 |

TABLE IV 12 ft³ Chamber; 37° C.; 30% $H_2O_2$

| Flow (ft³/hr) | Time (hrs) to reach steady state for desired % chamber saturation | | | |
|---|---|---|---|---|
| | 12.5 | 25 | 50 | 90 |
| 1 | 1.60 | 3.45 | 8.32 | 27.63 |
| 5 | 0.32 | 0.69 | 1.66 | 5.53 |
| 10 | 0.16 | 0.35 | 0.83 | 2.76 |
| 15 | 0.11 | 0.23 | 0.55 | 1.84 |
| 20 | 0.08 | 0.17 | 0.42 | 1.38 |
| $H_2O_2$ Vapor Concentration (mg/l) | 0.58 | 1.15 | 2.30 | 4.14 |

Partial levels of saturation (e.g. 12.5%, 25%, 50%, and 90%) are used to prevent unwanted condensation of the vapor phase hydrogen peroxide on a surface which may be slightly cooler than the temperature used to calculate the hydrogen peroxide vapor injection rate. The data appearing in Tables I through IV may be used in the following manner. From Table I, assuming an air flow rate of ten ft³/hr, the maximum flow rate of a 30% hydrogen peroxide solution would be 72.4 mg/min. Assuming a six ft³ chamber, and a desired chamber saturation of 50%, from Table III we learn that at an air flow rate of ten ft³/hr it will take .42 hours for the chamber to reach 50% saturation. This is the time period which is calculated at step 80. Of course, if certain parameters are kept constant such as the temperature of the air stream Ts and concentration of the aqueous hydrogen peroxide, tables similar to Tables I through IV may be generated and stored in the microprocessor's memory. In that case, the calculation steps may be reduced to measuring the air flow F and picking appropriate values from the stored tables. This manner of operation is considered to be well within the skill of one of ordinary skill in the art such that no further discussion thereof is considered necessary.

At step 82, the time period during which the chamber is maintained at the desired percent of saturation is looked up. This time period will be input by the user and is dependent upon several factors including the nature of the undesirable organisms to be destroyed, the tolerance of the desirable organism to hydrogen peroxide if exposed thereto, the estimated time it will take hydrogen peroxide vapor to reach a desirable organism held in a container having a tortuous path, or the estimated time it will take hydrogen peroxide vapor to reach a desirable organism held within a container having a hydrogen peroxide filter.

The presence of hydrogen peroxide and/or the derivative free hydroxyl radical (—OH) in tissue cultures has been shown to be implicated in chromatid damage. Jones, et al., Influence of Added Catalase on Chromosome Stability and Neoplastic Transformation of Mouse Cells in Culture, *British Journal of Cancer* 52, pages 583-590, 1985. It is the intention of this invention to utilize very low levels of hydrogen peroxide vapor under controlled conditions, thereby preventing any diffusion of the vapor into the tissue culture media or condensation of the vapor and subsequent mixing with the media in question. The hydrogen peroxide vapor will be kept in the enclosure only long enough to ensure decontaminated or sterile surfaces. Thereafter, the vapor is flushed out of the enclosure with room air or sterile, humidified air. If the tortuous pathways of the culture flasks are not adequate to maintain a barrier to the hydrogen peroxide vapor, then flasks incorporating hydrogen peroxide filters or absorptive pathways which will allow only essential gases to enter and exit the flasks should be used.

Hydrogen peroxide vapor resistant plant cells may be disinfested/decontaminated by the present invention since low oxidant concentration and low temperatures can be utilized. It is anticipated that large numbers of different types of plant cells may ultimately prove resistant to hydrogen peroxide vapor. This is based in part on the fact that certain plants have metabolic pathways which normally dispose of hydrogen peroxide which the plant cells may come into contact with. Additionally, it is known that plant cells have rigid walls. Finally, if plant cells can withstand the harsh chemicals presently used to disinfest them, it is anticipated that they will withstand the minimal exposure to low concentrations of vapor phase hydrogen peroxide necessary for disinfestation.

As a precaution, however, where cells will be exposed to hydrogen peroxide vapors, then experimentation with individual cultures to determine safe exposure times may be desirable if literature discussing exposure times is not available. One technique which may be used to determine safe exposure times is set forth in Test Nos. 8 and 9, hereinbelow, in the section of this disclosure entitled "Experimental Results." However, it is noted that because only low levels of hydrogen peroxide vapor are required for decontamination or even sterilization (0.5-10 mg/l) and since the decontamination method of the present invention is a low temperature process (ambient to 80° C.), the present invention may be utilized to decontaminate or sterilize surfaces on or near many kinds of living cells without harming the cells.

The time which is looked up at step 82 may be stored in the microprocessor's memory or may be entered by the user through input device 44. This time is added to the time required for the chamber to obtain the desired degree of concentration, and a timer internal to the microprocessor 44 is set in a known manner to that total time at step 84.

At step 86 the microprocessor 42 opens valve 32 an amount necessary to achieve the flow rate of liquid hydrogen peroxide determined at step 78.

After the valve 32 has been opened, the microprocessor 42 may monitor at step 88 various process parameters to insure the process is being carried out as desired. These monitoring steps may include reading the temperature Tv to insure that the vaporization grid 36 is maintained at the proper temperature, reading the temperature Ts to insure the temperature of the air stream remains constant, reading the flow signal F to insure that the flow rate of air remains constant, or performing any other desired monitoring functions. Occasionally during the monitoring of the various functions, the timer will be checked at decision step 90 to determine if the time period set at step 84 has expired. If the time has not expired, the microprocessor may continue to monitor various process parameters. If the time period has expired, valve 32 will then be closed at step 92.

With the valve 32 closed at step 92, the timer is reset at step 94. The time period loaded into the timer at step 94 is the time period during which the pump 22 is operative but the valve 32 is closed. This time period should be sufficient to flush the incubator 10 of vapor phase hydrogen peroxide until the employee exposure level to hydrogen peroxide vapors is below approximately one part per million. The microprocessor 42 at decision step 96 determines if the time period being timed out by the timer has expired. When the time period has expired, the microprocessor 42 turns pump 22 off at step 98 which represents the end of the program.

Figure 3:
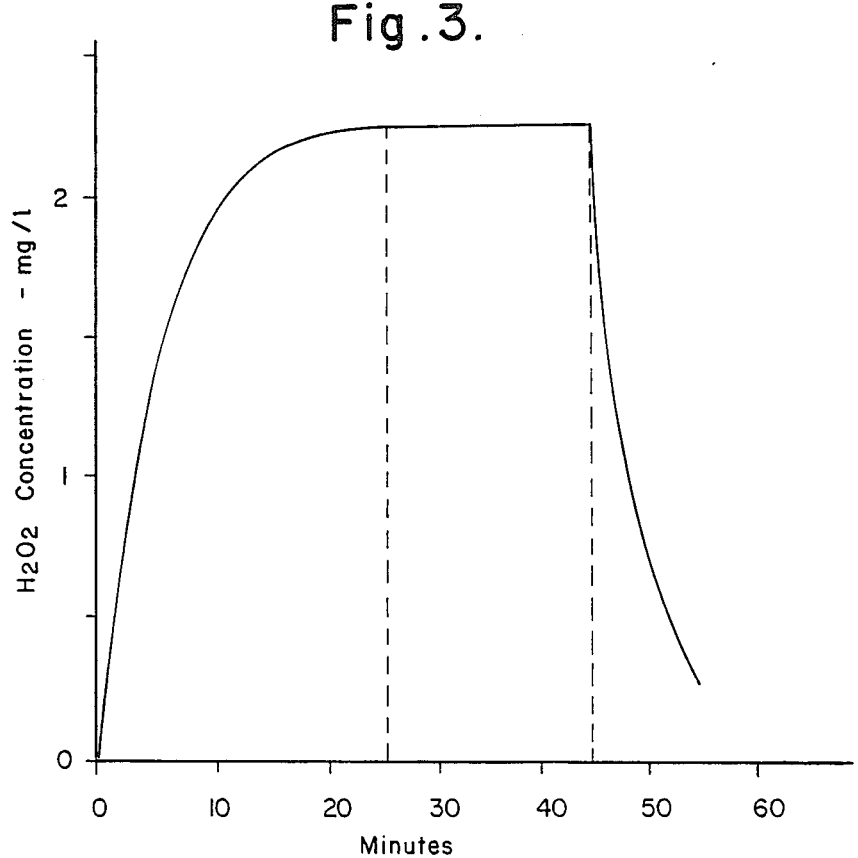
FIG. 3 is a graph illustrating vapor phase hydrogen peroxide concentrations as a function of time.

Turning to FIG. 3, a profile illustrating the vapor phase hydrogen peroxide concentration within the incubator 10 as a function of time is illustrated. Assuming an air flow rate of ten $ft^3$/hr., we learn from Table I that the flow rate of liquid hydrogen peroxide solution onto the vaporization grid is 72.4 mg/min. Assuming a six $ft^3$ chamber, we learn from Table III that at an air flow rate of ten $ft^3$/hr it will take .42 hours (25.2 minutes) to reach the desired chamber saturation of 50%. After the desired chamber saturation has been reached, assume that that degree of saturation is to be maintained for twenty minutes to insure sterilization. Thereafter, valve 32 is closed while pump 22 remains operative for a period of ten minutes to flush the vapor phase hydrogen peroxide from the incubator. The profile illustrated in FIG. 3 is a graphic representation of the aforementioned conditions.

The profile illustrated in FIG. 3 is only one example of the virtually limitless ways in which the method of the present invention may be performed. The time required to reach the desired percent saturation of the chamber as well as the time spent at that degree of saturation will depend upon such factors as the air flow rate, chamber size, apparatus used to prevent hydrogen peroxide vapor from contacting tissue cultures, tolerance of the tissue cultures to hydrogen peroxide vapor, etc.

Experimental Results

Figure 4:
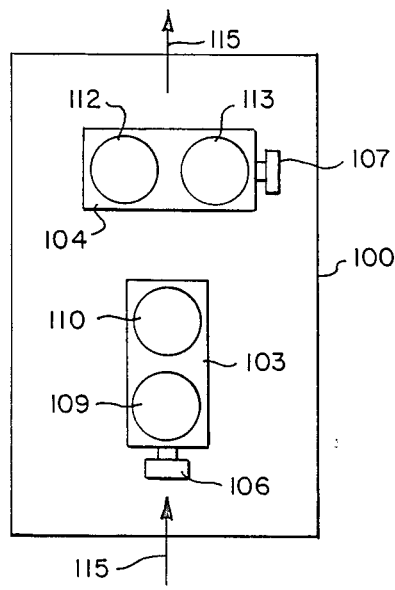
FIG. 4 illustrates an incubator which was used to test the efficacy of the present invention.

A test chamber 100 was set up as illustrated in FIG. 4 to test the efficacy of the present invention. The test chamber was loaded with a first 103 and a second 104 seventy five $cm^2$ polystyrene tissue culture flasks each having a canted neck. The flasks were filled with fifty ml of distilled water. Caps 106 and 107 of the flasks 103 and 104, respectively, were screwed on tightly and then backed off one-half turn in order to provide a tortuous path for the vapor phase hydrogen peroxide. The water was preheated to approximately 37° C. by microwaving for ten to twenty seconds.

The flask 103 carried a closed petri dish 109 and an open petri dish 110. Similarly, the flask 104 carried a closed petri dish 112 and an open petri dish 113. The petri dishes were five cm diameter glass dishes each containing ten ml of water.

The test chamber was operated with a flow of fifteen ft$^3$/hr in the direction indicated by the arrows 115. The chamber was maintained at a temperature of approximately 37° C. while the vaporizer was operated at a temperature of 97° C. Using a temperature Ts of the air stream of 37° C. and an air flow F of fifteen ft$^3$/hr., and a 30% hydrogen peroxide solution, we learn from Table I that the flow rate of aqueous hydrogen peroxide is 108.6 mg/min. This results in a maximum vapor phase hydrogen peroxide concentration of 4.6 mg/l.

Spore coupons (*Bacillus subtilis var niger*) were prepared according to the following procedure. A $10^6$ dilution of stock suspension was prepared from an American Sterilizer Company 100380 GL stock (HS population $6.7 \times 10^9$/ml). The dilution was heat shocked for twenty minutes at 80° C. A $10^4$ dilution was made and then ten microliters were taken from each dilution and placed on separate polystyrene coupons having an area of one cm$^2$. Coupons having populations of $10^2$ and $10^4$ spores were thus prepared. The coupons were air dried overnight prior to use.

Open petri dishes 109 and 113 each contained a coupon having a $10^2$ population, a coupon having a $10^4$ population, and a suture loop used to monitor bleaching during the cycle. The closed petri dishes 112 and 110, as well as the flasks 103 and 104, contained nothing more than the water previously mentioned.

Test No. 1

In the first test, a fifteen minute cycle time was used. During the fifteen minute cycle time, the vaporizer was used to produce hydrogen peroxide vapor for approximately eight of the fifteen minutes. Seven minutes were therefore allowed for aeration of the chamber before the door was opened. In the eight minute time period 0.53 g of hydrogen peroxide were delivered to the vaporizer. Thus, the rate of hydrogen peroxide introduction was 0.53g/8 mins, or 66.25 mg/min. The maximum hydrogen peroxide vapor concentration achieved in the air stream in this experiment was 2.8 mg/l, although as much as 4.6 mg/l could have been introduced without causing condensation of the vapor phase hydrogen peroxide. Thus, the rate at which vapor phase hydrogen peroxide was introduced was 61% of the maximum rate.

After the test was conducted, the water in two of the four petri dishes and in each of the flasks was analyzed to determine the hydrogen peroxide concentration in each container. This was accomplished spectrophotometrically by measuring the reaction of hydrogen peroxide with xylenol orange at an absorption of 525nm. The results are summarized in table V herein below.

TABLE V

| Container | Dil'n | A525 | H$_2$O$_2$ Conc (mg/l) |
|---|---|---|---|
| Flask 103 | 10° | 0.00 | 0.00 |
| Flask 104 | 10° | 0.17 | 0.09 |
| Closed Dish 109 | 10° | 0.258 | 1.52 |
| Closed Dish 112 | 10$^{-1}$ | 0.068 | 4.00 |

The coupons having $10^2$ spore populations and the coupons having the $10^4$ spore populations positioned in the petri dishes 110 and 113 were all sterile.

The results of this test clearly demonstrate that a closed flask such as flasks 103 and 104 can have its exterior surfaces sterilized in situ according to the method of the present invention so as to destroy harmful bacteria on the outside of the flask. Harmful bacteria on all inside surfaces of the incubator 100 are also destroyed as are airborne contaminants within the incubator 100 without adversely affecting tissue cultures within the flasks.

Test No. 2

The test previously described was run again using a thirty minute cycle time. With a thirty minute cycle time, the vaporizer was operative for approximately twenty-two minutes with eight minutes being reserved for aeration. 1.29 g of hydrogen peroxide were delivered in the twenty-two minutes of operation of the vaporizer such that the delivery rate was 58.64 mg/min. This delivery rate was 54% of the maximum rate at saturation. The amount of hydrogen peroxide absorbed by the water within the various containers is illustrated hereinbelow in Table VI.

TABLE VI

| Container | Dil'n | A525 | H$_2$O$_2$ Conc (mg/l) |
|---|---|---|---|
| Flask 103 | 10° | .083 | 0.46 |
| Flask 104 | 10° | .036 | 0.21 |
| Closed Dish 109 | 10$^{-1}$ | .300 | 17.6 |
| Closed Dish 112 | 10$^{-1}$ | .227 | 13.4 |

Table VI clearly illustrates that minimal amounts of hydrogen peroxide were found in the water within the flasks 103 and 104. As with the previous experiment, all four test coupons indicated that complete sterilization had been achieved.

Test Nos. 3, 4, and 5

Additional tests were performed in an effort to determine the minimum contact time required to sterilize the spore-inoculated coupons within the chamber and to measure the amount of hydrogen peroxide dissolving into the water inside the tissue culture flasks 103 and 104. These tests were carried out at a flow rate F of fifteen ft$^3$/hr. and an air stream temperature Ts of 37° C. Both the flasks 103 and 104 were facing forward into the hydrogen peroxide flow. The delivery rate for three different cycle times is illustrated below in table VII.

TABLE VII

| Cycle Time | 30% H$_2$O$_2$ | Total gms Sol'n | Amount Del'vrd (mg/min) | Max. H$_2$O$_2$ Vapor Conc. (mg/l) |
|---|---|---|---|---|
| 15 min. | H$_2$O$_2$ off at 8 min. | 0.87 | 108.7 | 4.3 |
| 12 min. | H$_2$O$_2$ off at 5 min. | 0.53 | 106.0 | 3.7 |
| 10 min. | H$_2$O$_2$ off at 3 min. | 0.28 | 93.3 | 2.5 |

The amount of hydrogen peroxide dissolved into the water within the flasks 103 and 104 is summarized in Table VIII hereinbelow.

TABLE VIII

| Cycle Time | Flask | Dil'n | A525 | H$_2$O$_2$ Conc. (mg/l) |
|---|---|---|---|---|
| 15 min. | 103 | 10° | 0.099 | 0.59 |
| 15 min. | 104 | 10° | 0.103 | 0.61 |
| 12 min. | 103 | 10° | 0* | 0 |

TABLE VIII-continued

| Cycle Time | Flask | Dil'n | A525 | $H_2O_2$ Conc. (mg/l) |
|---|---|---|---|---|
| 12 min. | 104 | 10° | 0 | 0 |
| 10 min. | 103 | 10° | 0 | 0 |
| 10 min. | 104 | 10° | 0 | 0 |

For all cycle times and all flask locations the spore coupons (containing populations of $10^2$ and $10^4$ spores) were sterilized. Thus, even a cycle time as short as ten minutes, wherein hydrogen peroxide is injected over a three minute period, and wherein only 93.3 mg/min. were delivered, resulted in complete sterilization of the area surrounding the flasks while no detectable amount of hydrogen peroxide was absorbed by the water within the flasks.

Test Nos. 6 and 7

Two additional tests were carried out in an effort to determine if spore populations as high as $10^6$ spores could be destroyed. The previously described tests were rerun for ten and fifteen minute cycles using coupons having the aforementioned higher spore populations. Table IX hereinbelow illustrates the delivery rate of hydrogen peroxide.

TABLE IX

| Cycle Time | 30% $H_2O_2$ | Sol. Used (gms) | Rate (mg/min) | Max. $H_2O_2$ Vapor Conc. (mg/l) |
|---|---|---|---|---|
| 15 min. | $H_2O_2$ off at 8 | 0.72 | 90.0 | 3.5 |
| 10 min. | $H_2O_2$ off at 3 | 0.29 | 96.7 | 2.7 |

The amount of hydrogen peroxide dissolved into the water within the flasks 103 and 104 is summarized in Table X hereinbelow.

TABLE X

| Cycle Time | Flask | Dil'n | A525 | $H_2O_2$ Conc. (mg/l) |
|---|---|---|---|---|
| 15 min. | 103 | 10° | .093 | 0.57 |
| 15 min. | 104 | 10° | .190 | 1.16 |
| 10 min. | 103 | 10° | 0 | 0 |
| 10 min. | 104 | 10° | 0 | 0 |

For each of the two cycle times, all spore coupons were sterilized. Thus, a cycle time as short as ten minutes wherein hydrogen peroxide is injected for three minutes resulted in sterilization of the area outside of the flasks without any detectable amounts of hydrogen peroxide being absorbed by the water within the flasks.

In summary, the tests performed clearly demonstrate that the method of the present invention can be used to sterilize the outside of containers holding tissue cultures, the inside surface area of the enclosure, and the air within the enclosure while partially opened flasks holding tissue cultures are in place. Hydrogen peroxide concentrations and cycle times can be controlled to insure complete sterilization without affecting the tissue cultures. The present invention thus represents a substantial advance over the prior art wherein no such in situ sterilization could be performed.

Test Nos. 8 and 9

To determine the effects of two different hydrogen peroxide concentrations (0.1 and 10.0 mg/l aqueous) tests were performed on mouse ascites tumor cells. Six tubes (4 ml in each) containing RPMI 1640 medium with $10^6$/ml of mouse ascites tumor cells were prepared. A .1 ml portion of the cells was centrifuged at 500 rpm for ten minutes. The medium was decanted off with a Pasteur pipette. One drop of Trypan blue stain was added to the cells and mixed with only the dead cells picking up the stain. The aforementioned concentrations of aqueous hydrogen peroxide were added to the tubes which were incubated at 37° C. During incubation the cells were continuously shaken to help them stay suspended and samples were removed every hour.

A small aliquot of the stained cells from the samples were placed in a haemocytometer and 500 cells were randomly counted to determine the number of dead ones in each of the tubes. This method of counting was also applied to a control tube. The experiments were performed in duplicate. Table XI illustrates the number of dead cells in each of the tubes containing the hydrogen peroxide, as well as the number of dead cells in the control tube, over various contact times.

TABLE XI

| Contact Time (Hrs.) | # of Dead Cells/500 Total | | |
|---|---|---|---|
| | 0.1 mg/l | 10.0 mg/l | Control |
| 0 | — | — | 9 |
| 1.5 | 4/10 | 21/14 | 29/5 |
| 2.5 | 6/7 | 30/70 | 10/10 |
| 3.5 | 8/10 | 106/297 | 7/5 |
| 4.5 | 9/4 | 432/415 | 8/4 |

Table XI clearly illustrates that exposure of the cells to 0.1 mg/l of hydrogen peroxide resulted in no more dead cells than those in the control tube. Conversely, exposure of the cells to 10.0 mg/l of hydrogen peroxide clearly resulted in substantially large numbers of dead cells. Thus, it would appear that for this particular type of cell, maintaining the hydrogen peroxide concentration at a level less than 0.1 mg/l would not result in the destruction of the tissue cultures. As illustrated in Tables V, VIII, and X, various cycle times and hydrogen peroxide concentrations may be used which are sufficient for sterilization and yet which maintain hydrogen peroxide concentration levels less than the desired 0.1 mg/l.

Tables XII and XIII hereinbelow illustrate the hydrogen peroxide residuals in the tissue culture media.

TABLE XII

| Incubation Time (hrs) | Dil'n | 10 mg/l Initial A525 | Conc (mg/l) |
|---|---|---|---|
| 0 | $10^{-1}$ | .290 | 11.9 |
| 1 | $10^{-1}$ | .272 | 11.1 |
| 3 | $10^{-1}$ | .227 | 9.3 |
| 4 | $10^{-1}$ | .217 | 8.9 |
| 5 | $10^{-1}$ | .211 | 8.6 |

TABLE XIII

| Incubation Time (hrs) | Dil'n | 0.1 mg/l Initial A525 | Conc (mg/l) |
|---|---|---|---|
| 0 | 10° | .044 | 0.18 |
| 1 | 10° | .039 | 0.16 |
| 3 | 10° | .014 | 0.06 |
| 4 | 10° | .011 | 0.04 |
| 5 | 10° | .000 | 0.00 |

Summary

In summary, the present invention is for a method of selectively destroying organisms within a predetermined area. For example, by introducing vapor phase hydrogen peroxide into the predetermined area at a rate sufficient to reach a predetermined concentration, and by maintaining that concentration for a predetermined period of time, undesirable organisms on the outside of tissue culture flasks, on all interior surfaces of the incubator, and in the air space within the incubator are destroyed without harming the tissue cultures held within the flasks. This represents a substantial advance over the prior art wherein no such in situ sterilization could be performed. The apparatus 12 may be programmed to perform a decontamination cycle each time the door is closed to destroy undesirable organisms which enter when the door is open and to insure that the cultures remain contamination free. Alternatively, the decontamination cycle may be performed every day at a predetermined hour such as an early morning hour so as to not interfere with access to the incubator.

The present invention may be used in conjunction with animal cells which are maintained in flasks having either a tortous path or a hydrogen peroxide filter protecting the opening of the flask. The present invention may also be used for the decontamination/sterilization of the exterior surfaces of an organism such as an egg. The present invention may also be used in conjunction with plant cell cultures which, because of their higher tolerance to hydrogen peroxide, may be exposed directly thereto. In this manner, plant cell cultures may be disinfested in addition to the aforementioned benefits from sterilizing the surrounding environment.

While the present invention has been described in connection an exemplary embodiment thereof, it will be understood that many modifications and variations will be readily apparent to those of ordinary skill in the art. This disclosure and the following claims are intended to cover all such modifications and variations.

What we claim is:

1. A method of selectively destroying organisms within an enclosed predetermined area, comprising the steps of:
    introducing vapor phase hydrogen peroxide into the predetermined area at a rate sufficient to cause a predetermined concentration of hydrogen peroxide to be reached, regulating the temperature and pressure in said enclosed predetermined area to prevent any substantial change in pressure and to maintain the temperature above the dew point of hydrogen peroxide to prevent substantial condensation of the hydrogen peroxide within the predetermined area;
    maintaining said predetermined concentration for a period of time sufficient for destroying undesirable organisms and insufficient for harming desirable living cells in vitro; and
    removing said vapor phase hydrogen peroxide from the area after said period of time has elapsed.

2. The method of claim 1 wherein said step of introducing vapor phase hydrogen peroxide includes the steps of creating a flow of air through the predetermined area and injecting vapor phase hydrogen peroxide into said flow.

3. The method of claim 2 wherein said step of injecting vapor phase hydrogen peroxide includes the step of conveying aqueous hydrogen peroxide into a means for vaporizing.

4. The method of claim 3 additionally comprising the step of sensing the temperature of the flowing air, and wherein the rate at which said aqueous hydrogen peroxide is conveyed into said means for vaporizing is responsive to said sensed temperature.

5. The method of claim 4 further including the step of calculating a maximum rate of introduction of vapor phase hydrogen peroxide into the predetermined area based on said sensed temperature.

6. The method of claim 5 further including the step of ascertaining the concentration of said aqueous hydrogen peroxide, and including the step of adjusting the rate at which said aqueous hydrogen peroxide is conveyed into said means for vaporizing based on said ascertained concentration and said calculated maximum rate of introduction of vapor phase hydrogen peroxide.

7. The method of claim 2 wherein the step of removing vapor phase hydrogen peroxide includes the steps of maintaining the flow of air through the predetermined area and ending the injection of vapor phase hydrogen peroxide into the flow.

8. The method of claim 1 wherein said desirable living cells are held in containers each having a tortuous path at its opening, and wherein said step of maintaining the predetermined concentration includes the step of maintaining said predetermined concentration for a period of time sufficient for said vapor phase hydrogen peroxide to at least decontaminate the outside of said containers and insufficient for said vapor phase hydrogen peroxide to travel said tortuous paths and reach said living cells.

9. The method of claim 1 wherein said desirable living cells are held in containers each having a filter at its opening, and wherein said step of maintaining said predetermined concentration includes the step of maintaining said predetermined concentration for a period of time sufficient for said vapor phase hydrogen peroxide to at least decontaminate the outside of said containers and insufficient for said vapor phase hydrogen peroxide to penetrate said filters and reach said living cells.

10. The method of claim 1 wherein said desirable living cells are held in open containers, and wherein said step of maintaining said predetermined concentration includes the step of maintaining said predetermined concentration for a period of time sufficient for said vapor phase hydrogen peroxide to at least disinfest the exterior surfaces of said cells and insufficient for said vapor phase hydrogen peroxide to harm said desirable living cells.

11. A method of selectively destroying organisms within an enclosure having interior surfaces and enclosing a predetermined volume, said method comprising:
    inserting desirable living cells in vitro into said enclosure;
    at least decontaminating said interior surfaces of said enclosure and destroying airborne contaminants within said volume by introducing vapor phase hydrogen peroxide into the enclosure at a rate sufficient to cause a predetermined concentration of hydrogen peroxide to be reached, regulating the temperature and pressure in said enclosure to prevent any substantial change in pressure and to maintain the temperature above the dew point of hydrogen peroxide to prevent substantial condensation of the hydrogen peroxide within the enclosure;
    maintaining said predetermined concentration for a period of time sufficient for destroying undesirable organisms and insufficient for harming said desirable living cells in vitro; and removing said vapor phase hydrogen peroxide after said decontaminating step.

12. The method of claim 11 wherein the step of placing said desirable living cells into said enclosure comprises placing said desirable living cells in a container having a tortuous path at its opening, and wherein said decontaminating step includes decontaminating the exterior surfaces of said container.

13. The method of claim 11 wherein the step of placing said desirable living cells into said enclosure comprises placing said desirable living cells in a container having a filter at its opening, and wherein said decontaminating step includes decontaminating the exterior surfaces of said container.

14. The method of claim 11 wherein the step of placing said desirable living cells into said enclosure comprises placing said desirable living cells in an open container, and wherein said decontaminating step includes at least disinfesting the exterior surfaces of said living cells.

15. The method of claim 11 wherein said step of decontaminating includes the step of sterilizing said interior surfaces of said enclosure and destroying airborne contaminants within said volume.

16. The method of claim 11 wherein the step of inserting desirable living cells includes the step of inserting desirable living cells in vitro into an autoclave.

17. The method of claim 11 wherein the step of inserting desirable living cells includes the step of inserting desirable living cells in vitro into an incubator.

18. A method of selectively destroying organisms within an enclosed predetermined area, comprising the steps of:

establishing an air flow through said predetermined area;

measuring the temperature of said flowing air;

calculating the maximum rate of injection of vapor phase hydrogen peroxide into said predetermined area based on said measured temperature;

ascertaining the hydrogen peroxide concentration of a source of aqueous hydrogen peroxide;

calculating the liquid hydrogen peroxide flow rate needed to achieve a desired injection rate which is not greater than the calculated maximum injection rate of vapor phase hydrogen peroxide;

conveying said aqueous hydrogen peroxide into a means for vaporizing at said calculated flow rate;

maintaining said flow rate for a time period sufficient to establish a predetermined concentration of vapor phase hydrogen peroxide in said predetermined area and sufficient to maintain said predetermined concentration for a period of time sufficient to destroy undesirable organisms and insufficient to harm desirable living cells in vitro;

regulating the temperature and pressure in said enclosed predetermined area to prevent any substantial change in pressure and to maintain the temperature above the dew point of hydrogen peroxide to prevent substantial condensation of the hydrogen peroxide within said enclosed predetermined area;

ending the conveying of aqueous hydrogen peroxide into said means for vaporizing; and maintaining said air flow through said predetermined area for a period of time sufficient to remove said vapor phase hydrogen peroxide from said predetermined area.

* * * * *

UNITED STATES PATENT AND TRADEMARK OFFICE
CERTIFICATE OF CORRECTION

PATENT NO. : 4,863,688

DATED : September 5, 1989

INVENTOR(S) : William C. Schmidt and James R. Rickloff

It is certified that error appears in the above-identified patent and that said Letters Patent is hereby corrected as shown below:

Col. 8, in Table II, lines 12 and 13 beneath 20, insert --$H_2O_2$ Vapor Concentration (mg/1)--.

Col. 8, in Table II, line 13,
      insert --0.58-- beneath 0.02 under column 12.5,
      insert --1.15-- beneath 0.04 under column 25
      insert --2.30-- beneath 0.11 under column 50
      insert --4.14-- beneath 0.35 under column 90

Col. 11, line 20, after "population" and before 6.7 x 10 9/ml)., insert --(a hyphen)--

Col. 11, line 57, delete "table" and substitute therefor --Table--.

Col. 12, line 48, delete "table" and substitute therefor --Table--.

Col. 13, line 7, insert --* All zero absorptions were actually negative readings--.

Col. 13, line 20, delete "106" and substitute therefor --$10^6$--.

UNITED STATES PATENT AND TRADEMARK OFFICE
CERTIFICATE OF CORRECTION

PATENT NO. : 4,863,688

DATED : September 5, 1989

INVENTOR(S) : William C. Schmidt and James R. Rickloff

It is certified that error appears in the above-identified patent and that said Letters Patent is hereby corrected as shown below:

Col. 9, line 10, delete "et el," and substitute therefor --et al.--.

Col. 15, line 21, delete "tortous" and substitute therefor --tortuous--.

Col. 15, line 32, after "connection" insert --with--.

Signed and Sealed this

Twenty-fifth Day of June, 1991

Attest:

HARRY F. MANBECK, JR.

Attesting Officer

Commissioner of Patents and Trademarks